United States Patent
Carson et al.

(10) Patent No.: US 6,548,478 B2
(45) Date of Patent: Apr. 15, 2003

(54) VIRGINIAMYCIN MIXTURE

(75) Inventors: James W. Carson, New York, NY (US); Frederic W. Chapin, New York, NY (US); Charles H. Fahrenholz, New York, NY (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 10/038,309

(22) Filed: Oct. 24, 2001

(65) Prior Publication Data

US 2002/0082201 A1 Jun. 27, 2002

Related U.S. Application Data

(63) Continuation of application No. 09/829,852, filed on Apr. 10, 2001, now abandoned, which is a continuation of application No. 09/284,541, filed as application No. PCT/IB97/00643 on Jun. 5, 1997, now abandoned.
(60) Provisional application No. 60/020,512, filed on Jul. 1, 1996.

(51) Int. Cl.[7] .................. A61K 38/15; A61K 31/47
(52) U.S. Cl. ........................... 514/9; 514/310
(58) Field of Search .................. 514/9, 310, 375; 426/635, 807

(56) References Cited

U.S. PATENT DOCUMENTS

| 4,559,323 A | 12/1985 | Michel et al. |
| 5,221,693 A | 6/1993 | Shetty |
| 5,384,124 A | 1/1995 | Courteille et al. |

OTHER PUBLICATIONS

Merck Index, Merck & Co., 1989, 11th Edition, No. 9910, pp. 1574–1575.

Primary Examiner—Frederick Krass
Assistant Examiner—Donna Jagoe
(74) Attorney, Agent, or Firm—Peter C. Richardson; Gregg C. Benson; Martha G. Munchhof

(57) ABSTRACT

A mixture comprising:
  a) virginiamycin;
  b) a pharmaceutically acceptable and substantially anhydrous wetting agent including sodium lauryl sulfate;
  c) a sufficient amount of pharmaceutically acceptable buffering agent to provide a pH of from about 3 0 to about 7.0 when said mixture is added to water; and
  d) from about 0.5 weight percent to about 10 0 weight percent colloidal silicon dioxide,
  wherein the ratio of the weight percent of (b) to the weight percent of (a) percent by weight is at least about 1.5:1.

The mixture is designed to be added to water to produce a stable suspension of the virginiamycin, which can then be applied to, for example, feed grain.

45 Claims, No Drawings

VIRGINIAMYCIN MIXTURE

The present application is a continuation of U.S. application Ser. No. 09/829,852 filed Apr. 10, 2001, now abandoned which is a continuation of U.S. application Ser. No. 09/284,541 filed Jan. 8, 1999, now abandoned, which represents the U.S. National Stage of International application PCT/IB97/00643, itself internationally filed Jun. 5, 1997, which claims priority, as does the present application, to U.S. provisional application No. 60/020,512, filed Jul. 1, 1996. The complete text and claims of the 09/829,852 application are incorporated by reference herein, as if fully set forth.

BACKGROUND OF THE INVENTION

The present invention relates to a mixture comprising virginiamycin

Virginiamycin antibiotics, in their most effective form, include both M and S components. Coccito, *Micro Rev.*, 43, 145 (1979). Virginiamycin has been used as an antibacterial and in the prevention of lactic acidosis (e.g. U.S. Pat. Nos. 5,137,900 and 5,242,938 and The Merck Index, 12th Edition, pages 1707–1708). It has also been used in the form of a feed additive to improve growth in poultry, swine, and cattle. A possible mechanism for its use as a growth promotant could relate to an inhibition of intestinal flora. Coccito, supra. Virginiamycin's widely accepted use stems from having low toxicity, minimal production of resistant mutant strains, quick degradation in feces, and minimal tissue retention.

Wettable powders have been used for the administration of various insecticides and herbicides.

SUMMARY OF THE INVENTION

The present invention relates to a mixture comprising:
a) virginiamycin;
b) a pharmaceutically acceptable surfactant including sodium lauryl sulfate;
c) a sufficient amount of pharmaceutically acceptable buffering agent to provide a pH of from about 3.0 to about 7.0 when said mixture is added to water, and
d) from about 0.5 weight percent to about 10.0 weight percent colloidal silicon dioxide, wherein the ratio of the weight percent of (b) to the weight percent of (a) is at least about 1.5:1.

DETAILED DESCRIPTION

The mixture comprising virginiamycin is in the form of a wettable-type powder. The powder mixture can be added to water, including some forms of hard water to produce a stable suspension of the virginiamycin, which can then be, for example, dilivered directly to a patient (e.g orally) or applied to, for example, food stuffs such as feed grain. The feed grain is then fed to animals for example livestock and poultry thereby administering the virginiamycin The mixture should preferably be substantially anhydrous so as to maximize the shelf life of the mixture prior to forming the water suspension.

Virginiamycin can be produced using known methods, for example fermentation. For example, virginiamycin M can be produced by fermentation of a streptomyces species originally isolated from Indian soil samples and deposited with the American Type Culture Collection, 12301 Parklawn Drive, Rockville, Md. 20852, United States of America on Jul. 29, 1986 and assigned ATCC number 53527 U.S. Pat. No. 5,242,938.

Dose levels of virginiamycin are known in the art and can vary due to a number of factors, including, for example, compound activity, the route of administration, the time of administration, disease severity, excretion rate, combination of other drugs, as well as the age, body weight, sex, diet, and general health of the patient being treated. Generally, for example, with a human subject, the daily effective dose can range from about 1.0 mg to about 1500 mg, preferably about 10 mg to about 500 mg, in single or divided doses. For a domestic animal, the effective dose can range from about 5 to about 200 parts per million per volume of food. U.S. Pat. No. 5,242,938.

For veterinary purposes, dosage levels known in the art can also be found, for example, in the 1996 Feed Additive Compendium, Miller Publishing Co. (1996), pp 324–328.

The claimed mixture comprises virginiamycin, preferably substantially pure, and a pharmaceutically acceptable surfactant, sodium lauryl sulfate (SLS), preferably substantially anhydrous and granulated. The ratio of the weight percent of SLS to the weight percent of virginiamycin should be at least about 1.5 to 1, preferably about 1.54 to 1. Substantially pure virginiamycin has an activity of about 200% (plus or minus 20%) as measured by methods known in the art (Gossele, et al., *Analyst*, 116, 1373 (1991) and Blain, et al., *Analyst*, 119, 361 (1994).

The powder mixture also includes a pharmaceutically acceptable anti-caking agent, colloidal silicon dioxide, which can act as scavenger for water as well as a wetting and suspending agent for the virginiamycin. The amount of colloidal silicon dioxide can range from 0.5 weight percent of the mixture to about 10.0 weight percent of the mixture, preferably about 2.0 weight percent.

A pharmaceutically acceptable buffer is also included, for example phosphate or citrate buffers, preferably citric acid/sodium citrate. The amount of buffer should be sufficient to provide a pH of from about 3.0 to about 7.0, preferably from about 4.0 to about 5.5 when the mixture is added to water. Maintenance of pH permits the virginiamycin to be suspended in a water environment with minimal effect on its activity The powder mixture is added to water to form a stable suspension of the virginiamycin, which is then applied to, for example, feed grain. The amount of mixture dispensed in the water is approximately 4.5% by weight of the suspension.

A pharmaceutically acceptable water soluble filler material can also be included. Examples include sugars, such as lactose and dextrose, preferably lactose. Such fillers may also effect the flowability of the mixture.

A pharmaceutically acceptable anti-foaming agent, which is, for example, an emulsion and will not substantially effect the pH of the resulting suspension, can also be included in the anhydrous mixture, for example, polydimethylsiloxane. Once the suspension is made, the anti-foaming agent minimizes the amount of foam caused by the SLS upon agitation of the suspension. This can be important if, for example, the suspension is being sprayed and a pump is needed to drive the suspension through the spraying apparatus. The amount of anti-foaming agent in the mixture can range from about 0.5 weight percent to about 10.0 weight percent, preferably about 2.8 weight percent.

The mixture should preferably be maintained as substantially anhydrous prior to forming the suspension in order to minimize the breakdown of the components of the mixture.

As a result of minimizing breakdown, the shelf life of the mixture can be maximized.

The mixture is formed by adding its ingredients together and thoroughly blending them together. Once the mixture is formed, a suspension can be made by adding the mixture to water. The resulting suspension is substantially stable with minimal sedimentation of virginiamycin falling out of the suspension for about a day with periodic stirring or with little or no stirring of the suspension for about a couple hours, preferably about six hours once the suspension has been properly formed.

A pharmaceutically acceptable indicator dye can also be included, depending upon acceptable food and drug regulations. The dye, for example, FD&C blue No. 1 powder, would give a blue color to the suspension and, in turn, to feed grain sprayed herewith Thus, the treated grain can be readily identified.

A preferred formulation of the claimed invention is the following.

| INGREDIENT | FORMULA | % W/W |
|---|---|---|
| Virginiamycin Feed Grade* (activity = about 200%) | not available | 18.8 |
| Sodium Lauryl Sulfate | $C_{12}H_{25}NaO_4S$ | 30.0 |
| Colloidal Silicon Dioxide | $SiO_2$ | 2.0 |
| Citric Acid, anhydrous, fine granular | $C_6H_8O_7$ | 20.0 |
| Sodium Citrate anhydrous powder | $C_6H_5N_{23}O_7$ | 20.0 |
| Antifoam AF emulsion | $[-(CH_3)_2SiO_2]_n$ | 2.8 |
| FD&C Blue No. 1 powder | FDA Lot #AG4275 Warner-Jenkinson Co. Code #05601 | 0.4 |
| Lactose* anhydrous, 80 mesh | $C_{12}H_{22}O_{11}$ | 6.0 |

Virginiamycin and lactose calculated to provide 40% virginiamycin activity. Amounts will vary depending on purity of virginiamycin.

The following are intended as non-limiting examples of the present invention.

EXAMPLE 1

The below listed ingredients were combined and mixed together until a uniform mixture was formed.

| INGREDIENT | % w/v | AMOUNT |
|---|---|---|
| Virginiamycin Feed Grade 213% | 0.94 | 9.40 g |
| Sodium Lauryl Sulfate | 1.50 | 15.00 g |
| Colloidal Silicon Dioxide | 0.10 | 1.00 g |
| Citric Acid U.S.P. | 1.00 | 10.00 g |
| Sodium Citrate U.S.P. | 1.00 | 10.00 g |
| Antifoam A.F. | 0.10 | 1.00 g |

A suspension was formed by adding the above mixture to 900 ml of distilled water in a 1 liter graduated cylinder until dispersion was complete. Then additional water was added to bring the total volume to 1 liter. pH 4.24.

EXAMPLE 2

The below listed ingredients were combined and mixed together until a uniform mixture was formed.

| INGREDIENT | % w/v | AMOUNT |
|---|---|---|
| Virginiamycin Feed Grade 213% | 0.94 | 9.40 g |
| Sodium Lauryl Sulfate | 1.50 | 15.00 g |
| Colloidal Silicon Dioxide | 0.10 | 1.00 g |
| Citric Acid U.S.P. | 1.00 | 10.00 g |
| Sodium Citrate U.S.P. | 1.00 | 10.00 g |
| Antifoam A.F. | 0.10 | 1.00 g |

A suspension was formed by adding the above mixture to 900 ml of distilled water in a 1 liter graduate until dispersion was complete. Then additional water was added to bring the total volume to 1 liter. pH 4.30.

EXAMPLE 3

The below listed ingredients were placed in a mixer and mixed for 15 minutes to form a base mixture.

| INGREDIENT | % w/v | AMOUNT |
|---|---|---|
| Sodium Lauryl Sulfate | 36.9 | 4500.0 g |
| Citric Acid | 24.6 | 3000.0 g |
| Sodium Citrate | 24.6 | 3000.0 g |
| Anhydrous Lactose, 80 Mesh (Sheffield) | 7.4 | 900.0 g |
| Antifoam A. F. Emulsion | 3.4 | 420.0 g |
| Colloidal Silicon Dioxide | 2.6 | 300.0 g |
| FD&C Blue No. 1 Powder | 0.5 | 60.0 g |

A. 1126.8 g of virginiamycin animal feed grade (213% activity) (18.8%) was added to 4873.2 g of base mixture (81.2%) in a mixer and mixed for 15 minutes.

B. 956.1 g of virginiamycin animal feed grade (205% activity) (19.5%) was added to 3943.2 g of base mixture (80.5%) in a mixer and mixed for 15 minutes.

What is claimed is:

1. A mixture comprising:

a) virginiamycin;

b) a pharmaceutically acceptable surfactant;

c) a sufficient amount of a pharmaceutically acceptable buffering agent to provide a pH of from about 3.0 to about 7.0 when said mixture is added to water; and d) from about 0.5 weight percent to about 10.0 weight percent colloidal silicon dioxide, wherein the ratio of the weight percent of (b) to the weight percent of (a) is at least about 1.5:1.

2. The mixture of claim 1, wherein the ratio of (b) to (a) is about 1.54:1.

3. The mixture of claim 1, wherein the amount of buffer is sufficient to provide a pH of from about 4.0 to about 5.5 when said mixture is added to water.

4. The mixture of claim 1, wherein said buffer is selected from the group consisting of citric acid and sodium citrate.

5. The mixture of claim 4, wherein said citric acid and sodium citrate are substantially anhydrous.

6. The mixture of claim 1, further including a pharmaceutically acceptable anti-foaming agent.

7. The mixture of claim 6, wherein said anti-foaming agent is polydimethylsiloxane.

8. The mixture of claim 1, further including a pharmaceutically acceptable dye.

9. The mixture of claim 1, wherein said virginiamycin is substantially pure.

10. The mixture of claim 1 wherein said mixture is substantially anhydrous.

11. A substantially anhydrous mixture comprising:
a) virginiamycin;
b) a pharmaceutically acceptable and substantially anhydrous surfactant;
c) a sufficient amount of a pharmaceutically acceptable buffering agent to provide a pH of from about 3.0 to about 7.0 when said mixture is added to water; and
d) from about 0.5 weight percent to about 10.0 weight percent colloidal silicon dioxide,
wherein the ratio of the weight percent of (b) to the weight percent of (a) is at least about 1.5:1.

12. The anhydrous mixture of claim 11, wherein the ratio of (b) to (a) is about 1.54:1.

13. The anhydrous mixture of claim 11, where the amount of buffer is sufficient to provide a pH of from about 4.0 to about 5.5 when said mixture is added to water.

14. The anhydrous mixture of claim 11, wherein said buffer is selected from the group consisting of substantially anhydrous citric acid and substantially anhydrous sodium citrate.

15. The anhydrous mixture of claim 11, further including a pharmaceutically acceptable anti-foaming agent.

16. The anhydrous mixture of claim 15, wherein said anti-foaming agent is polydimethylsiloxane.

17. The anhydrous mixture of claim 11, further including a pharmaceutically acceptable dye.

18. The anhydrous mixture of claim 11, wherein said virginiamycin is substantially pure.

19. A substantially anhydrous mixture comprising:
a) virginiamycin;
b) a pharmaceutically acceptable and substantially anhydrous surfactant;
c) a sufficient amount of a pharmaceutically acceptable buffering agent to provide a pH of from about 3.0 to about 7.0 when said mixture is added to water;
d) from about 0.5 weight percent to about 10.0 weight percent colloidal silicon dioxide;
e) a pharmaceutically acceptable anti-foaming agent; and
f) a pharmaceutically acceptable dye,
wherein the ratio of the weight percent of (b) to the weight percent of (a) is at least about 1.5:1.

20. The anhydrous mixture of claim 19, wherein the ratio of (b) to (a) is about 1.54:1.

21. The anhydrous mixture of claim 19, where the amount of buffer is sufficient to provide a pH of from about 4.0 to about 5.5 when said mixture is added to water.

22. The anhydrous mixture of claim 19, wherein said buffer is selected from the group consisting of substantially anhydrous citric acid and substantially anhydrous sodium citrate.

23. The anhydrous mixture of claim 19, wherein said anti-foaming agent is polydimethylsiloxane.

24. The anhydrous mixture of claim 19, wherein said virginiamycin is substantially pure.

25. Feed grain treated with a water suspension of a mixture comprising:
a) virginiamycin;
b) a pharmaceutically acceptable surfactant;
c) a sufficient amount of a pharmaceutically acceptable buffering agent to maintain said suspension at pH of from about 3.0 to about 7.0;
d) from about 0.5 weight percent to about 10.0 weight percent colloidal silicon dioxide,
wherein the ratio of the weight percent of (b) to the weight percent of (a) is at least about 1.5:1.

26. The feed grain of claim 25, wherein the ratio of (b) to (a) is about 1.54:1.

27. The feed grain of claim 25, where the amount of buffer is sufficient to provide a pH of from about 4.0 to about 5.5 in said suspension.

28. The feed grain of claim 25, wherein said buffer is selected from the group consisting of citric acid and sodium citrate.

29. The feed grain of claim 28, wherein the citric acid and sodium citrate is substantially anhydrous.

30. The feed grain of claim 25, said mixture further including a pharmaceutically acceptable dye.

31. The feed grain of claim 25, wherein said virginiamycin is substantially pure.

32. The feed grain of claim 25, further including a pharmaceutically acceptable anti-foaming agent in said mixture.

33. The feed grain of claim 32, wherein said antifoaming agent is polydimethylsiloxane.

34. A method of treating feed grain with virginiamycin, comprising
(1) forming a mixture including:
a) virginiamycin,
b) a pharmaceutically acceptable surfactant,
c) a sufficient amount of a pharmaceutically acceptable buffering agent to provide a pH of from about 3.0 to about 7.0 when the mixture is added to water, and
d) from about 0.5 weight percent to about 10.0 weight percent colloidal silicon dioxide,
wherein the ratio of the weight percent of (b) to the weight percent of (a) is at least about 1.5:1;
(2) suspending the mixture in water to form a suspension; and
(3) applying the suspension to feed grain.

35. The method of claim 34, wherein the ratio of (b) to (a) in said mixture is about 1.54:1.

36. The method of claim 34, wherein the amount of buffer in said mixture is sufficient to provide a pH of from about 4.0 to about 5.5 when said mixture is added to water.

37. The method of claim 34, wherein said buffer in said mixture selected from the group consisting of citric acid and sodium citrate.

38. The method of claim 37, wherein said citric acid and sodium citrate are substantially anhydrous.

39. The method of claim 34, further including a pharmaceutically acceptable anti-foaming agent in said mixture.

40. The method of claim 39, wherein said anti-foaming agent is polydimethylsiloxane.

41. The method of claim 34, further including a pharmaceutically acceptable dye in said mixture.

42. The method of claim 34, wherein said virginiamycin in said mixture is substantially pure.

43. The method of claim 34, wherein said mixture is substantially anhydrous.

44. The method of claim 34, wherein said applying step includes spraying the feed grain with said suspension.

45. The method of claim 34, further including drying the feed grain after the applying step.

* * * * *